(12) United States Patent
Gianakos

(10) Patent No.: US 6,790,199 B1
(45) Date of Patent: Sep. 14, 2004

(54) NEEDLE PROTECTIVE ASSEMBLY FOR MULTI-DRAW NEEDLE

(75) Inventor: Art Gianakos, Loudonville, NY (US)

(73) Assignee: North American Medical Products, Inc., Albany, NY (US)

( * ) Notice: Subject to any disclaimer, the term of this patent is extended or adjusted under 35 U.S.C. 154(b) by 76 days.

(21) Appl. No.: 09/768,397

(22) Filed: Jan. 24, 2001

Related U.S. Application Data

(63) Continuation-in-part of application No. 09/672,341, filed on Sep. 28, 2000, now abandoned.

(51) Int. Cl.[7] .............................................. A61M 5/32
(52) U.S. Cl. ........................................ 604/197; 604/162
(58) Field of Search ................................. 604/162, 163, 604/192, 197, 198

(56) References Cited

U.S. PATENT DOCUMENTS

| | | | | |
|---|---|---|---|---|
| 4,300,678 A | * | 11/1981 | Gyure et al. ................. | 206/364 |
| 4,373,526 A | * | 2/1983 | Kling ........................... | 604/117 |
| 4,681,567 A | * | 7/1987 | Masters et al. ............... | 604/198 |
| 4,752,290 A | * | 6/1988 | Schramm ..................... | 604/198 |
| 4,790,827 A | * | 12/1988 | Haber et al. ................. | 604/198 |
| 4,871,355 A | * | 10/1989 | Kikkawa ...................... | 604/198 |
| 4,921,491 A | * | 5/1990 | Champ ......................... | 604/199 |
| 4,976,701 A | * | 12/1990 | Ejlersen et al. .............. | 604/192 |
| 4,981,469 A | * | 1/1991 | Whitehouse et al. .......... | 604/86 |
| 5,131,405 A | * | 7/1992 | Burns ........................... | 600/576 |
| 5,195,993 A | * | 3/1993 | Gianakos ...................... | 604/523 |
| 5,290,255 A | * | 3/1994 | Vallelunga et al. ........... | 604/197 |
| 5,312,347 A | * | 5/1994 | Osborne et al. .............. | 604/110 |
| 5,415,648 A | * | 5/1995 | Malay et al. ................. | 604/181 |
| 5,498,241 A | * | 3/1996 | Fabozzi ........................ | 604/177 |
| 5,498,243 A | * | 3/1996 | Vallelunga et al. ........... | 604/197 |
| 5,735,823 A | * | 4/1998 | Berger ......................... | 604/192 |
| 5,964,739 A | * | 10/1999 | Champ ......................... | 604/263 |
| 6,024,727 A | * | 2/2000 | Thorne et al. ................ | 604/195 |
| 6,280,401 B1 | * | 8/2001 | Mahurkar ..................... | 600/576 |
| 6,309,376 B1 | * | 10/2001 | Alesi ............................ | 604/263 |
| 2002/0165498 A1 | * | 11/2002 | Ward ........................... | 604/198 |
| 2003/0050608 A1 | * | 3/2003 | Brown .......................... | 604/198 |
| 2003/0060772 A1 | * | 3/2003 | Swenson ...................... | 604/183 |
| 2003/0163063 A1 | * | 8/2003 | Higaki et al. ................ | 600/576 |
| 2003/0171695 A1 | * | 9/2003 | Zurcher ........................ | 600/577 |

* cited by examiner

*Primary Examiner*—Brian L. Casler
*Assistant Examiner*—Jeremy Thissell
(74) *Attorney, Agent, or Firm*—Cohen, Pontani, Lieberman & Pavane

(57) ABSTRACT

A needle protective assembly in which a slidable sheath is mounted over a barrel which, in turn, encircles a needle. The sheath is adapted to slide along the barrel, and cover the needle after use, protecting against accidental needlesticks. The inner barrel is integrally formed with a hub in which the needle is mounted, and which may be used to attach the inventive protective assembly to a blood collection vial holder, or a hypodermic syringe, depending upon the application. In some embodiments, the protective assembly may also be formed integrally with either the blood collection vial holder, or the hypodermic syringe.

1 Claim, 7 Drawing Sheets

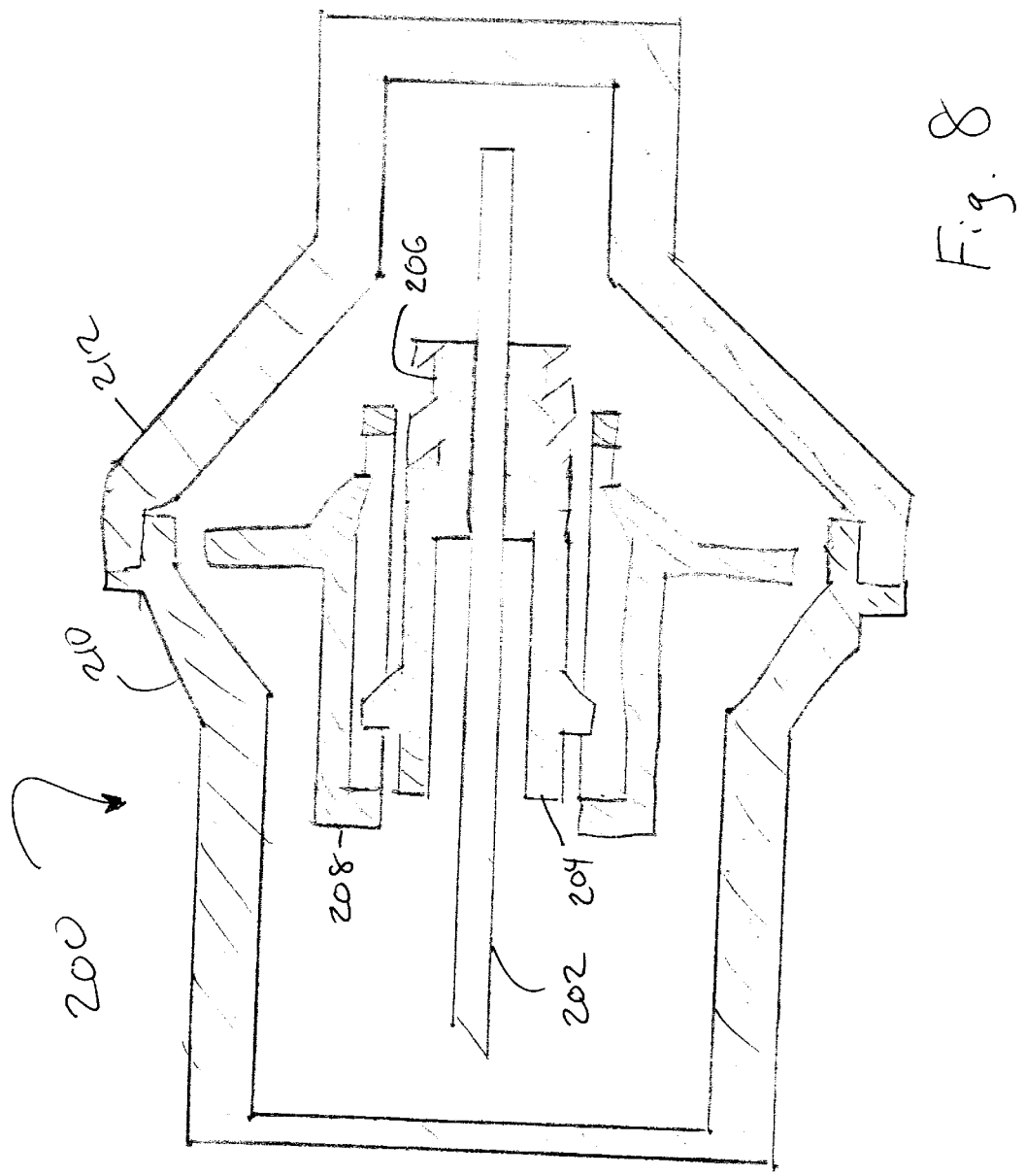

NEEDLE PROTECTIVE ASSEMBLY FOR MULTI-DRAW NEEDLE

CROSS-REFERENCE TO RELATED APPLICATION

This application is a continuation-in-part of my prior filed application, Ser. No. 09/672,341, filed Sep. 28, 2000, now abandoned.

BACKGROUND OF THE INVENTION

1. Field of the Invention

This invention relates to the field of protective devices used in health care, and, more particularly, to a needle protective assembly for needles used for collecting blood from, or dispensing medication to, a patient. The assembly includes a protective cover for covering the tip of a needle used with the assembly, after usage, to avoid accidental needlesticks.

2. Description of the Related Art

Over the last few years, there has been a widely reported surge in the occurrence of diseases which are communicable by the transmission of bodily fluids. This has caused a growing concern among healthcare professionals about the inadvertent transmission of disease by the accidental sticking of one's self with a contaminated needle, thereby causing the healthcare professional to be at risk when handling contaminated needles.

My prior patent, U.S. Pat. No. 5,195,993, disclosed a needle protecting assembly for use with hypodermic syringes. The disclosure of my prior patent is hereby incorporated herein by reference. In that patent, I disclose a needle protective assembly useful with traditional hypodermic needles. The assembly includes a slidable sheath which moves along a hypodermic needle to lockingly cover the tip, and thereby prevent accidental needlesticks. The patented device is useful, but not in every application which involves the use of needles for piercing the human body.

In my co-pending application, I disclose a needle protective assembly for a butterfly wing IV blood collection and scalp vein set, which is useful primarily in specific applications involving long-term attachment of a needle to a patient' s vein. This device, too, has utility, but does not cover all possible uses of medical needles.

For example, one area which has been underserved by the prior art is the field of multi-draw needles used for drawing several vials of blood from a patient with only one needlestick. In these applications, a blood collection tube holder is fitted with a needle for drawing blood. A vial for holding blood drawn from the patient is placed in the blood collection tube holder. The top of the vial includes a self-sealing rubber top which is pierced by the end of the needle opposite the end which is inserted into the patient. The needle conducts blood from the patient into the vial. If more than one vial of blood is required, the first vial may be removed, and replaced by a second vial, without removing the needle from the patient's vein, thereby reducing the amount of trauma suffered by repeated needlesticks, and avoiding scarring.

The medical professional drawing blood in this fashion has the same imperative to avoid an accidental needlestick and prevent infection as the user of the mentioned devices, but the prior devices may not be suitable for all applications.

One aspect of my first invention disclosed in U.S. Pat. No. 5,195,993 was that it had a relatively large profile, or outer diameter. This limited its applicability in some applications.

The butterfly device disclosed in my above-referred co-pending application addresses this issue, and reduces the overall profile of the needle protective assembly, but it, too, does not have utility in all applications due to its overall configuration, and specific applicability to an IV blood collection and scalp vein set.

Neither invention is targeted to the particular problems encountered in the field of multi-draw blood collection assemblies, in which the smaller overall profile is desired, with the ability to connect to a larger blood collection tube.

One product has been sold to that market, a part of the SAFE-POINT line of blood collection needles (Models M-D and VAC) sold by North American Medical Products, Inc. In this product, a needle protecting assembly of a slightly reduced size (compared to that disclosed in my original patent) is used in a multi-draw blood collection system. In this assembly, a standard blood collection needle is press-fit into a two-piece protective assembly. The standard needle is purchased with the needle held inside a protective plastic cover, to avoid accidental needlesticks prior to use. The protective plastic cover is then broken off, and discarded. After use, the medical professional moves a slidable outer sheath over a fixed barrel from a retracted position in which the needle is exposed, into an extended position in which the needle is covered. This configuration has a slightly reduced profile but it is not sufficiently reduced for some applications.

Additionally, the prior devices suffer from the drawback that they require assembly before use, and it would be useful to provide a simple unitary device capable of being used without the need to attach a needle to another device, so that it may be manufactured more easily and less expensively.

SUMMARY OF THE INVENTION

It is therefore an object of the invention to provide a needle protective assembly having a reduced profile compared to prior devices.

It is a further object of the invention to provide a needle protective assembly which may be manufactured easily and conveniently.

Briefly stated, the invention is directed to a needle protective assembly in which a slidable sheath is mounted over a barrel which, in turn, encircles a needle. The sheath is adapted to slide along the barrel, and cover the needle after use, protecting against accidental needlesticks. The inner barrel is integrally formed with a hub in which the needle is mounted, and which may be used to attach the inventive protective assembly to a blood collection vial holder, or a hypodermic syringe, depending upon the application. In some embodiments, the protective assembly may also be formed integrally with either the blood collection vial holder, or the hypodermic syringe.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings wherein like reference numerals delineate similar elements throughout the general views:

FIG. 7 is a detail of a second embodiment of the invention, in which the inventive assembly is formed integrally with a syringe assembly, and the needle is omitted for clarity.

FIG. 8 is a cross-section of a third embodiment of the invention, in which the entire inventive assembly is encapsulated with a two-piece protective cap.

DETAILED DESCRIPTION OF THE PRESENTLY PREFERRED EMBODIMENTS

Figure 1:
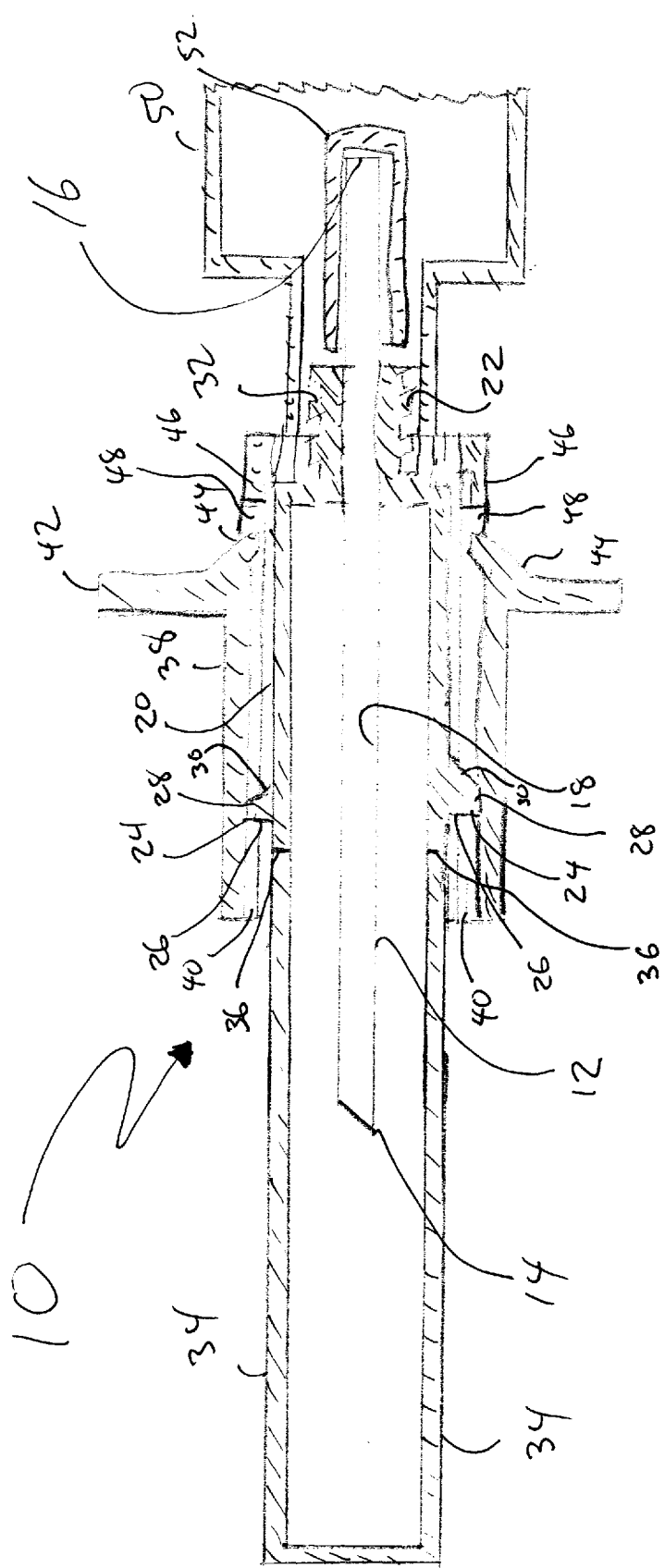
FIG. 1 is a cross-sectional view of the inventive needle protective assembly, before use.

A needle protective assembly 10 in accordance with the invention is shown in FIG. 1. Assembly 10 includes a hollow needle 12. Needle 12 defines a longitudinal axis of assembly 10 and includes a first end 14 which is extremely pointed and is the end which is inserted into the patient for dispensing medication or removing blood and a second, opposed, end 16. First end 14 is also the end which must be covered after usage to avoid accidental needlesticks. First end 14 is connected to second end 16 by a hollow lumen 18 which extends along the longitudinal axis of assembly 10.

Figure 6:
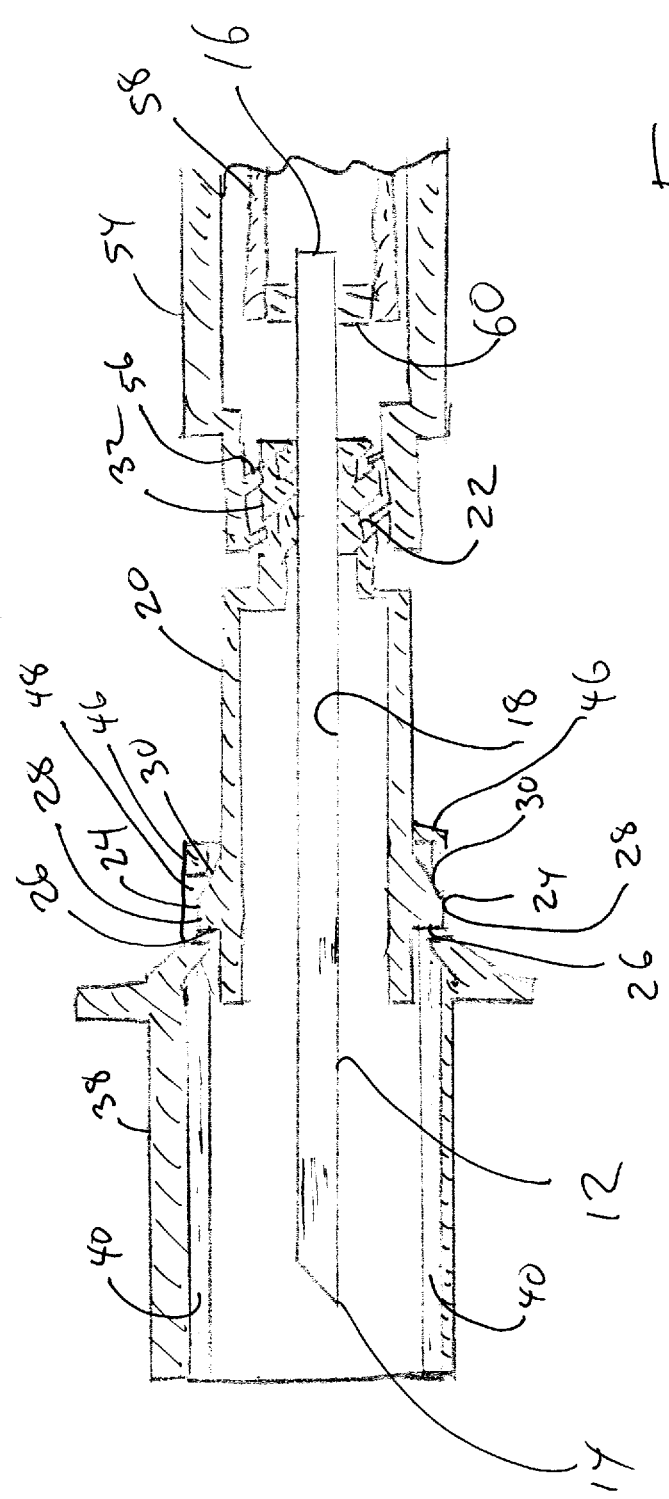
FIG. 6 is a cross-section of the assembly of FIG. 1, in which the movable sheath has been locked in place covering the tip of the needle after use, and also showing the connection of the inventive assembly to a blood collection vial.

A barrel 20 is securely mounted to needle 12 by a hub portion 22 thereof, disposed at the rear of barrel 20. Hub portion 22 is preferably integrally formed as part of barrel 20. Needle 12 extends into hub portion 22, but need not extend to the other side thereof, depending upon the application. In other words, second end 16 of needle 12 may be disposed within or at the end of hub portion 22, or, as shown in FIG. 1, it may extend past the end of hub portion 22. Barrel 20 further includes at least one angled shoulder or pawl 24 on one side thereof. In the preferred embodiment, barrel 20 would include two angled shoulders 24 on opposite sides of barrel 20, as shown in FIGS. 1 and 6.

Shoulder 24 includes a generally flat front side 26 extending axially from barrel 20, a flat top 28, and a sloped rear side 30. Rear side 30 need not be sloped, and may instead be generally parallel to front side 26, as a matter of design choice. The configuration of shoulder 24 may best be seen in FIG. 2 which is a detailed view of a portion of FIG. 1.

Figure 3:
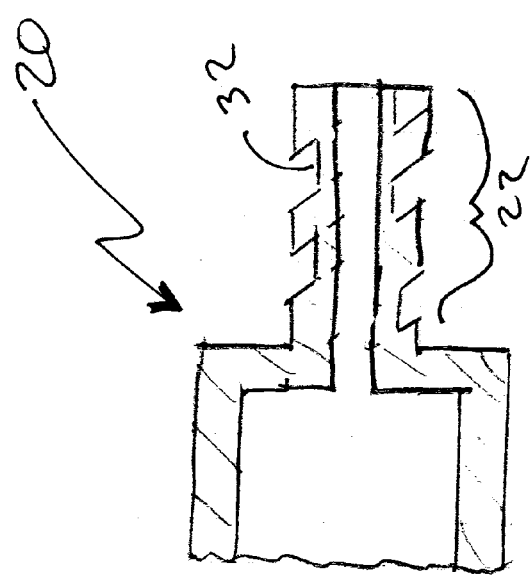
FIG. 3 is a detail of the hub section of the inventive assembly, showing its integral connection to the barrel of the assembly.

Hub portion 22 may include a threaded neck 32, depending upon the application, as will be described presently. As best shown in FIG. 3, threaded neck 32, hub portion 22 and barrel 20 are formed integrally as a single piece, permitting barrel 20 to be formed with a reduced diameter (profile). This reduced profile renders the device less expensive to manufacture, since it uses less material, and, more importantly, renders assembly 10 safer. The reduced diameter of barrel 20 makes it less possible for people with small fingers to stick themselves accidentally with needle 12 after usage, and allows for less movement of barrel 20 once locked in place, as described below.

Referring to FIG. 1, protective cap 34 is attached to barrel 20 at a frangible line 36. Protective cap 34 covers first end 14 of needle 12, and protects against accidental needlesticks prior to use of assembly 10.

Figure 4:
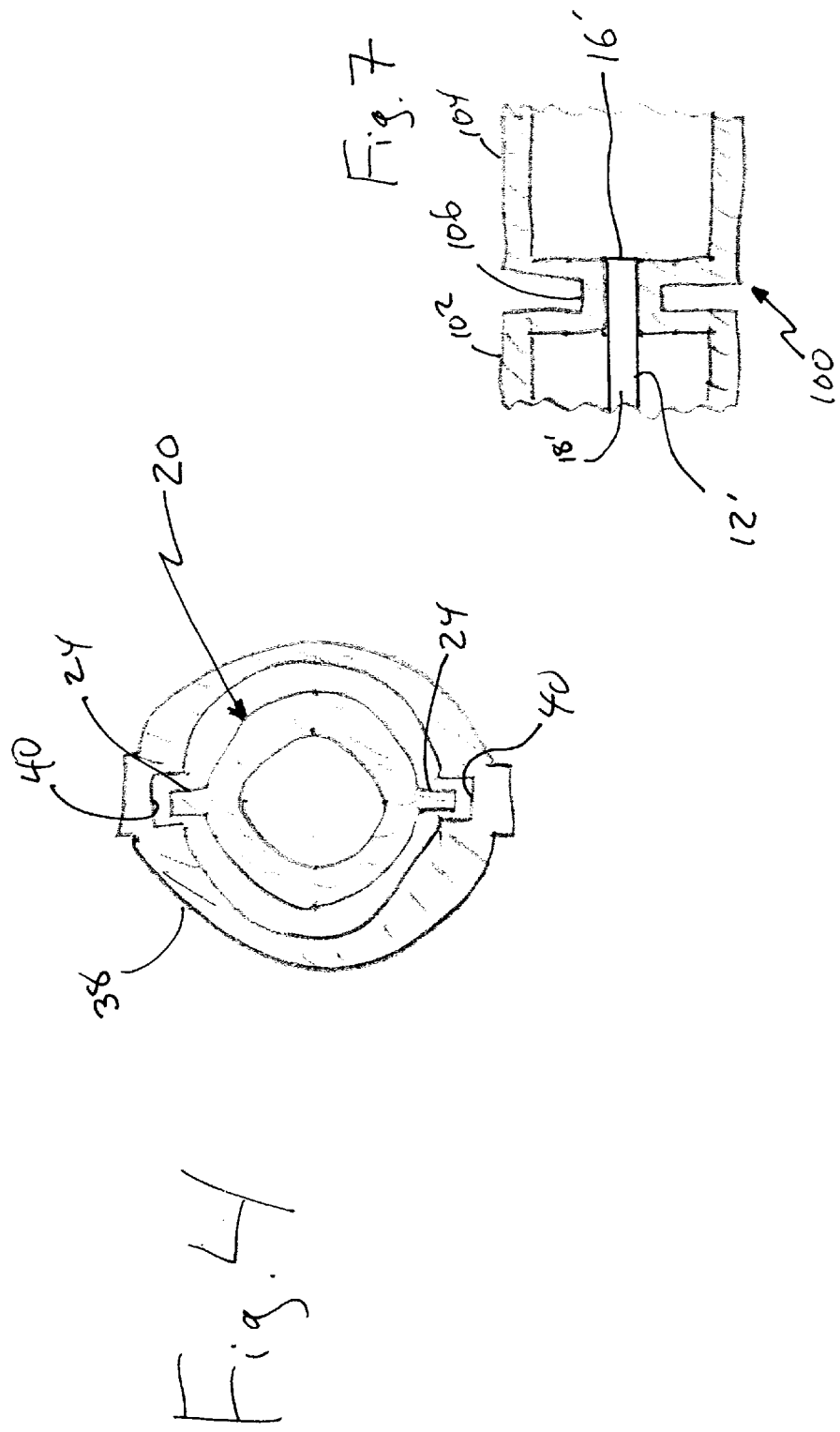
FIG. 4 is an end view of the assembly of FIG. 1, taken from the front end thereof, with the front protective cap, needle and flange omitted for clarity.

A sheath 38 is slidably mounted about barrel 20. Sheath 38 includes a slot 40, in which shoulder 24 is positioned. If assembly 10 includes two shoulders 24, then sheath 38 includes two respective slots 40. Slot 40 extends generally parallel to the longitudinal axis of needle 12, and constrains the sliding movement of sheath 38 along barrel 20 to be generally linear, i.e. with no twisting of sheath 38 as it travels the length of barrel 20. The positioning of shoulders 24 in slots 40 may also be seen in FIG. 4.

Figure 2:
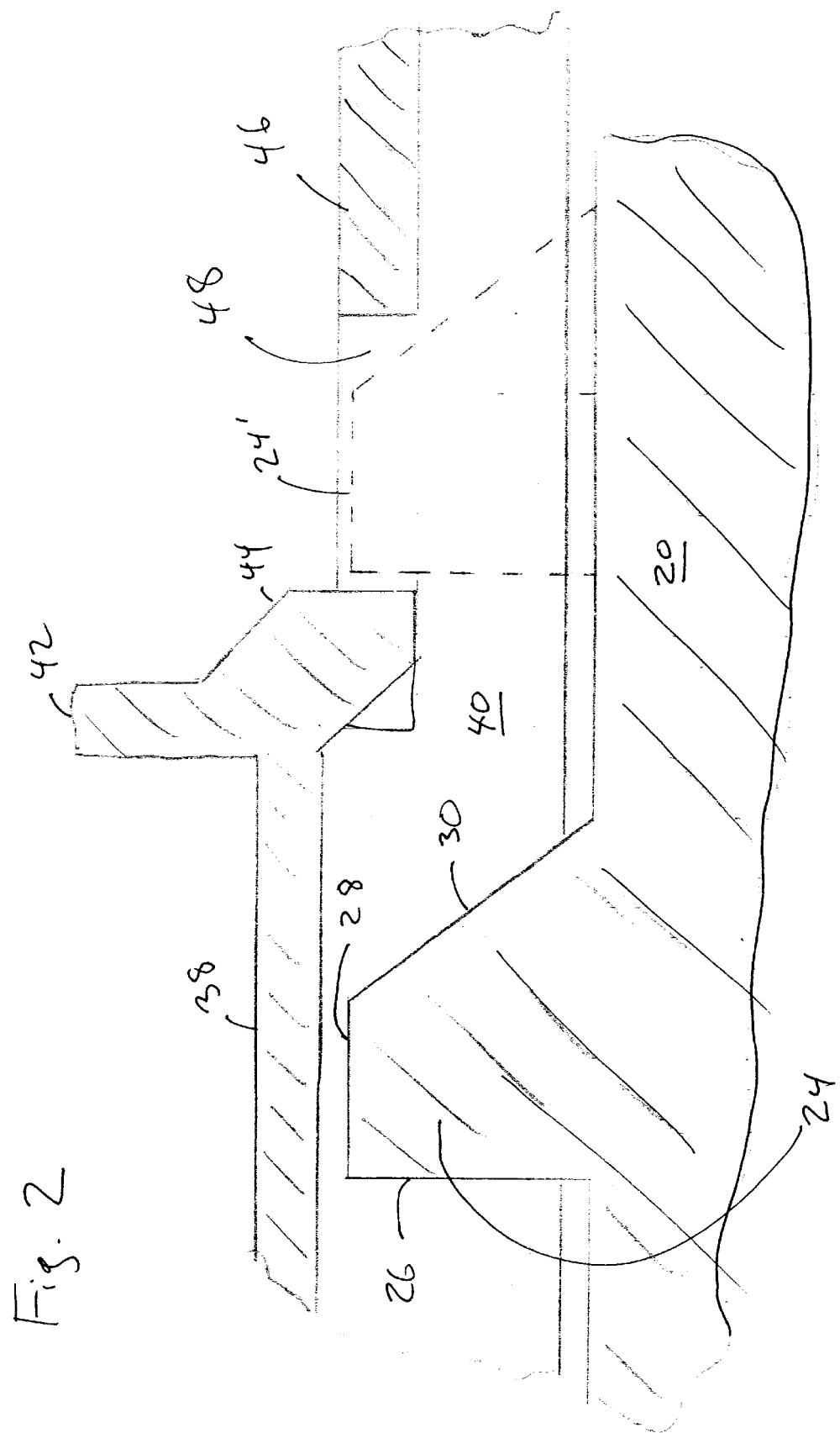
FIG. 2 is a detail of the view of FIG. 1, in which the locking assembly is shown in greater detail.
Figure 5:
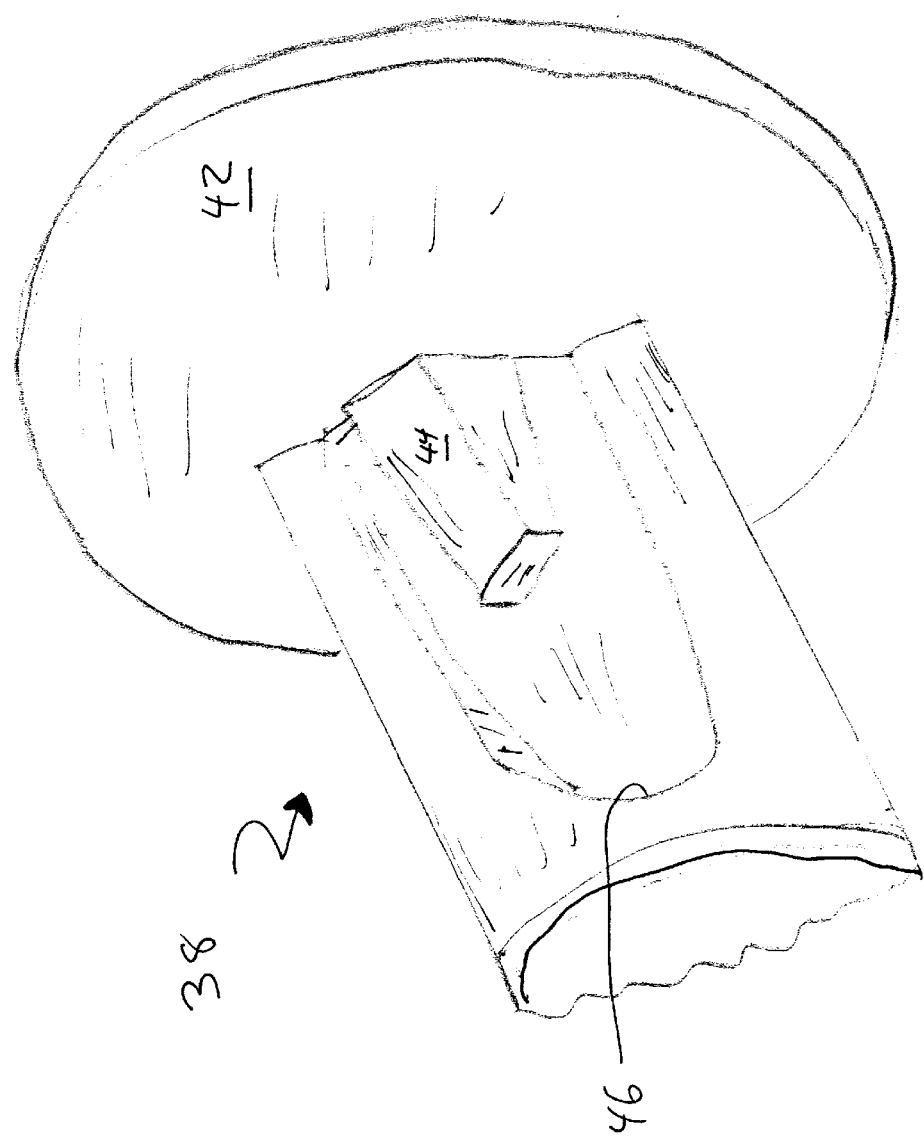
FIG. 5 is a further detail of the sheath of the assembly shown in FIG. 1, from a rear perspective, to illustrate the features thereof.

Sheath 38 further includes an annular flange 42, which may be used to slide sheath 38 along barrel 20. As best seen in FIGS. 2 and 5, a locking tab 44 projects downwardly and rearwardly from flange 42, into slot 40. The bottom of tab 44 is disposed at a height below that of top 28 of shoulder 24. A stop 46 is disposed at the rear of sheath 38, and at a height below top 28 of shoulder 24. Stop 46 is positioned a distance from tab 44, so that a gap 48 is formed between stop 46 and tab 44. Gap 48 is sized to be at least as large as top 28 of shoulder 24, and preferably only slightly larger than top 28.

A rear cap 50 is attached to hub portion 22 before usage, and a sleeve 52 may be placed about second end 16 of needle 12, for additional protection against accidental needlesticks before usage. Rear cap may be removably affixed to hub portion 22 in any desired fashion, such as, for example, by frictional seal, and sterile tape (not shown).

In operation, assembly 10 may simply and effectively protect against accidental needlesticks after usage. As shown in FIG. 6, assembly 10 may be used with a blood collection vial holder 54. After, the user removes rear cap 50 and sleeve 52 (Shown in FIG. 1), a threaded portion 56 of blood collection vial holder 54 is threaded onto threaded neck 32 of hub portion 22, so that blood collection vial holder 54 is securely mounted to barrel 20. The user will then place a blood collection vial 58 onto second end 16 of needle 12, by piercing a self-sealing rubber cap 60 at the head of blood collection vial 58, in known fashion.

To collect the blood, protective cap 34 is broken off at frangible line 36 (Shown in FIG. 1) exposing first end 14 of needle 12. First end 14 is then inserted into the patient for collecting blood, and blood travels through lumen 18, out second end 16 and into blood collection vial 58. If more than one vial of blood is desired, the user may stop the flow of blood into needle 12 by pressing on the patient's vein, and changing vials. This process is repeated as necessary, until a sufficient amount of blood is drawn. At that point, needle 12 is removed from the patient, exposing the user to the danger of accidental needlesticks with the contaminated first end 14 of needle 12. The user protects himself by pushing on flange 42 in a forward direction, causing sheath 38 to slide along barrel 20. The movement of sheath 38 along barrel 20 is linear, since the movement of sheath 38 is constrained by the co-operation of shoulder 24 in slot 40, until top 28 of shoulder of shoulder 24 contacts the bottom of tab 44. At this point, sheath 38 is still capable of returning to its original position, exposing (the now) contaminated first end 14 of needle 12.

To render assembly 10 safe, it is necessary for the user to continue pressing on flange 42, causing rear side 30 of shoulder 24 to contact the bottom of tab 44, and thereby deflect tab 44 upwards, sliding along top 28 of shoulder 24, until shoulder 24 reaches the position illustrated in dashed line as 24' in FIG. 2, wherein shoulder 24 will rest in gap 48 between tab 44 and stop 46. As described, the bottom of tab 44 and stop 46 are both disposed below top 28 of shoulder 24, so that shoulder 24 is securely locked into place. In this position, sheath 38 will now extend beyond first (contaminated) end 14 of needle 12, as shown in FIG. 6, protecting the user against accidental needlesticks.

This assembly permits the safe and efficient drawing of the patient's blood, and protects against accidental needlesticks after use. As stated, the reduced open diameter of sheath 38 compared to prior available protective devices renders assembly 10 less prone to accidental needlesticks, as well as cheaper to manufacture.

It will be appreciated by those of ordinary skill in the art that it is possible to utilize inventive assembly 10 with a standard hypodermic syringe, by merely changing threaded neck 22 to a standard luer lock, thereby enabling the connection of assembly 10 to a hypodermic syringe. It would also be possible to reverse the relative positions of shoulder 24 and gap 48, placing a pawl on sheath 38 and a notch in barrel 20 without departing from the scope of the invention described herein, so long as sheath 38 and barrel 20 may be locked in place, with sheath 38 extended past end 14 of needle 12, after use.

Not all applications in which there is concern with accidental needlesticks from contaminated needles involve blood collection. The dispensing of medication through standard hypodermic syringes is also a concern. In these applications, it is not necessary to provide for piercing a self-sealing stopper with an end of the needle. For dispensing medication, it is preferred that a second end 16' of a needle 12' not extend into a blood collection tube as shown in the embodiment of the invention shown in FIG. 7. In addition, it is possible to form an integral barrel/syringe 100 having a barrel portion 102, and a syringe portion 104 connected by a hub portion 106. End 16' of needle 12' may terminate within or at the end of hub portion 106. A sheath (not shown) may then be positioned identically to sheath 38 of the embodiment shown in FIGS. 1–6 on barrel portion 102.

In this embodiment, it is also possible to provide a single barrel/syringe assembly, pre-fabricated, to make assembly of the device easier in situ. In cases where a medication may need to be dispensed quickly, even the few seconds needed to put a needle assembly on a syringe may be critical (e.g. for dispensing snakebite anti-venom). Even in these time-critical applications, however, a protective cover for the needle may be provided, rendering the device safer after use, as well.

As noted above, reducing the overall diameter of the protective device is advantageous for many reasons. While the above-described device reduces the overall diameter of the protective sheath significantly, it may be possible to reduce it further. In the first embodiment, the provision of protective cap 34 within sheath 38 requires a certain amount of clearance between the two elements, to allow for lateral movement of protective cap 34 in the process of breaking it off barrel 20. In a third embodiment of the invention shown in FIG. 8 the use of a protective cap at the end of barrel 20 is eliminated, permitting an even smaller diameter barrel, and thus an even smaller diameter assembly overall. In the needle protective assembly 200, needle 202 is held within a barrel 204 having an integral hub 206. Hub 206 has a threaded portion for mating with a suitable blood collection device (not shown), or may have a luer lock (also not shown) for mating with a standard syringe. Otherwise barrel 204 is similar in shape and operation to barrel 20 of assembly 10, and co-operates with a sheath 208 which is, in turn, similar in shape and operation to sheath 38 of assembly 10. However, since assembly 200 lacks protective cap 34, the diameter of barrel 204 and sheath 208 may be significantly smaller than those of their counterparts.

Assembly 200 nonetheless requires some mechanism for protecting against accidental needlesticks before usage, as well as preserving the sterile nature of needle 202. Accordingly, a pair of mating encapsulating caps 210, 212 may be provided. Caps 210, 212 are configured to mate securely and maintain the integrity and safety of assembly 200, as shown.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A needle protective assembly comprising:

a hollow needle having a longitudinal axis, a first end and a second end, said second end being opposite to said first end along said longitudinal axis of said needle, said first end of said needle having a point for insertion of said needle into a patient;

a barrel having a longitudinal axis which lies substantially along said axis of said needle, a first end and a second end, said second end being opposite to said first end along said longitudinal axis of said barrel, said barrel further having a hub integrally molded therein, disposed at said second end of said barrel, said barrel substantially covering a portion of said needle removed from said first end of said needle, said hub being attached to said needle, and adapted to permit passage of said needle therethrough;

a sheath slidably mounted on said barrel, from a first position in which said point is exposed, to a second position in which said sheath substantially covers said point so as to prevent accidental needlesticks by said point of said needle; and a first removable cap for covering said first end of said needle when said sheath is in said first position;

wherein said needle extends beyond said hub, said first end of said needle is disposed on a first side of said hub, and said second end of said needle is disposed on a second side of said hub, opposite said first side of said hub; and said assembly further includes a second removable cap, covering said second end of said needle and adapted to mate with said first removable cap, and thereby encapsulate said sheath, said barrel, said needle and said hub.

* * * * *